United States Patent [19]
Heilmann et al.

[11] Patent Number: 5,478,466
[45] Date of Patent: Dec. 26, 1995

[54] CARTRIDGE FILTERS WITH INSOLUBLE ENZYME PARTICULATES CONTAINED THEREON

[75] Inventors: Steven M. Heilmann, Afton; Gary J. Drtina, Woodbury; Philip D. Eitzman, Woodbury; Louis C. Haddad, Mendota Heights; Frederick W. Hyde, New Brighton; Todd W. Johnson, Minneapolis, all of Minn.

[73] Assignee: Minnesota Mining and Manufacturing Company, St. Paul, Minn.

[21] Appl. No.: 427,281

[22] Filed: Apr. 21, 1995

Related U.S. Application Data

[63] Continuation of Ser. No. 106,412, Aug. 13, 1993, abandoned.

[51] Int. Cl.$^6$ ............................ B01D 36/00; B01D 27/00
[52] U.S. Cl. ........................ 210/205; 210/490; 210/491; 210/492; 210/500.25; 210/500.29; 210/500.36; 210/500.38; 210/493.5; 210/506; 210/416.1; 210/505; 210/508; 210/632; 210/502.1
[58] Field of Search ............................ 210/606, 632, 210/502.1, 503, 504, 505, 506, 507, 508, 500.25, 500.29, 500.36, 500.38, 490, 491, 492, 493.5, 416.1, 205

[56] References Cited

U.S. PATENT DOCUMENTS

| | | | |
|---|---|---|---|
| 3,058,594 | 6/1960 | Hultgren | 210/487 |
| 4,150,563 | 4/1979 | Minarik et al. | 73/61.1 C |
| 4,208,309 | 6/1980 | Kraemer et al. | 435/180 |
| 4,238,334 | 12/1980 | Halbfoster | 210/679 |
| 4,331,541 | 5/1982 | Akiyama et al. | 210/679 |
| 4,384,957 | 5/1983 | Crowder, III et al. | 210/656 |
| 4,404,285 | 9/1983 | Hou | 436/16 |
| 4,488,969 | 12/1984 | Hou | 210/679 |
| 4,663,163 | 5/1987 | Hou et al. | 424/101 |
| 4,774,004 | 9/1988 | Gruenewaelder et al. | 210/663 |
| 4,839,419 | 6/1989 | Kraemer et al. | 210/656 |
| 4,842,739 | 6/1989 | Tang | 210/489 |
| 4,857,461 | 8/1989 | Egerer et al. | 435/94 |
| 4,963,494 | 10/1990 | Hibino et al. | 210/632 |
| 4,966,707 | 10/1990 | Cussler et al. | 210/632 |
| 5,028,335 | 7/1991 | Sleytr et al. | 210/638 |
| 5,047,154 | 9/1991 | Comstock et al. | 210/636 |
| 5,051,184 | 9/1991 | Taylor | 210/632 |
| 5,155,144 | 10/1992 | Manganaro et al. | 523/134 |
| 5,310,688 | 5/1994 | Zale et al. | 436/535 |

FOREIGN PATENT DOCUMENTS 3406562  8/1985  Germany .

OTHER PUBLICATIONS

J. R. Ford, et al., *Biotechnol. & Bioeng. Symp. No. 3*, 1972, 267–284.
T. J. Harrington, et al., *Enzyme Microb. Technol.*, 1992, 14, 813–818.
Schmidt–Kastner, et al., *Biochem. Eng. [Intl. Congr.]*, 1986 (publ. 1987), 111–131.
A. M. Wilhelm and J. P. Riba, "Scale–Up and Optimization in Production Liquid Chromatography", *Journal of Chromatography*, 484(1989), 211–223.
Pierce 1989 Handbook and General Catalog, 1989, Pierce, p. 62, No. 20055.
Supelco Chromatography Products Catalog, 1994, Supelco, pp. 300 and 304; feature "P" (mesh support).

*Primary Examiner*—Robert A. Dawson
*Assistant Examiner*—Robert James Popovics
*Attorney, Agent, or Firm*—Gary L. Griswold; Walter N. Kirn; Lorraine R. Sherman

[57]  ABSTRACT

Insolubilized enzyme particulates are located on the upstream surface of a filtration layer of a filtering element which can be used in a cartridge filter. Employed in a recycling flow reaction system at relatively high flux rates, the cartridges are useful for conducting catalyzed chemical reactions of dissolved solutes, for example, esterifications, isomerizations, oxidations, reductions, and cyclizations.

32 Claims, 8 Drawing Sheets

CARTRIDGE FILTERS WITH INSOLUBLE ENZYME PARTICULATES CONTAINED THEREON

This is a continuation of application Ser. No. 08/106,412 filed Aug. 13, 1993, now abandoned.

FIELD OF THE INVENTION

This invention relates to novel filter elements containing insoluble enzyme particulates and to novel methods for their preparation. The particulate-loaded filter elements are useful in cartridge filters as catalysts for effecting chemical reactions of solutes in solutions subsequently passed through.

BACKGROUND OF THE INVENTION

Proteins are exceedingly versatile biomacromolecules. One class of proteins known as enzymes functions as perhaps nature's most perfect catalysts for effecting complex organic syntheses. Because enzymes function so efficiently at low concentrations causing a high conversion of reactants to products under extremely mild conditions of temperature and pH and do so with an incomparable degree of specificity (in terms of functional groups affected), they have long been sought after by organic chemists as catalysts to conduct chemical reactions. Medicinal and pharmaceutical chemists have further been intrigued by the ability of enzymes to synthesize just one of the possible optical isomers of a compound wherein the simple spatial arrangement of four different substituents on a particular carbon atom gives rise to unique pharmacological behavior. Interest in enzymes for synthetic purposes has also heightened recently by advances in molecular genetics that have allowed for the preparation of specific enzymes in a highly purified state, on a relatively large scale, and at substantially reduced cost.

Insolubilization of enzymes without losing catalytic activity has been an objective of many investigators because of the very practical advantages that catalyst systems can be easily removed from reaction mixtures by simple filtration and, at least in principle, can be reused many times. Other factors which contribute to cost savings of insolubilized enzyme catalysts over soluble enzymes and are normally accrued in the insolubilization process include enhanced stability over a wider range of temperature and pH.

The most common technique of employing immobilized or insolubilized enzymes to catalyze a chemical reaction is to simply add the insoluble particulates to a solution containing dissolved reactant. The insoluble catalyst is stirred, often at high rates, to facilitate reaction by more efficiently mixing catalyst and reactants. This stirring often causes mechanical breakup of the insoluble enzyme particulates which can give rise to leaching, enzyme deactivation, and increased separation costs, as smaller particulates are generally more difficult to remove from the reaction mixture. Also, if pH control is maintained by simultaneous addition of strong acid or base, the insolubilized enzyme will almost certainly be exposed to momentary pH extremes before the titrant can mix into the reaction mixture. In aqueous solution amino acid residues such as lysine, aspartic acid, glutamic acid, and others ultimately define protein structure because they are frequently charged and present on the periphery of the protein's tertiary structure. Sudden changes in pH can either protonate or deprotonate groups on these amino acid residues.

The above-mentioned deficiencies of batchwise employment of an insoluble enzyme as a heterogeneous component in a reaction mixture have led to the development of various flow reactors employing packed columns of insoluble enzyme particulates. While these reaction systems minimize mechanical instability, problems of modest capacity and pH instability remain. Catalyst capacity generally corresponds directly with column length, and with longer columns undesirably high pressures are required in order to achieve reasonably rapid throughput of solution. Also, pH control is generally completely lacking within the column where deleterious effects on the enzyme can occur.

Liquid cartridge filters have been developed over the years that operate at relatively high flow rates, e.g., liters per minute, and at relatively low pressures. In tangential flow or radial membrane cartridge filters, the filtering element is presented in a plane parallel to the liquid stream flow, and two effluents or permeates are produced, one filtered or processed by passing through the filtering element and another not. While these filter arrangements operate at low pressures and the unprocessed permeate can in theory be recycled, these systems are intrinsically more complicated and slower to completely process a liquid stream because of relatively low flow through the element; also, if modified to insolubilize enzymes, complete conversion of reactant would be required in one pass through the element.

In "dead end" filters the filtering element is presented perpendicularly to the direction of flow of the liquid stream. All the liquid stream is required to pass through the element and only one permeate is produced. Considered as a reactor in which reaction is occurring on or within the filtering element, the dead end cartridge filter would be analogous to a very wide, but short column. Because the actual length of the catalyst layer is relatively short, changes in pH caused by the enzymatic reaction should not be large at relatively high solution throughput. At high flow rates single pass conversion may be relatively low but by repeatedly cycling the effluent high conversion could be achieved, with pH being adjusted between passes. Attributes of recirculation to minimize diffusional effects, at least in analytical assays involving immobilized enzymes, are discussed by J. R. Ford, et al., *Biotechnol. & Bioeng. Symp. No. 3*, 1972, 267–284.

T. J. Harrington, et al., *Enzyme Microb. Technol.*, 1992, 14, 813–818 describe a ceramic microfilter employed in a recycling dead end configuration in which an alumina microfilter (0.45 micrometer nominal filter rating) has been activated with aminosilane/glutaraldehyde to accommodate enzyme attachment.

Efforts to improve capacity and lower operating pressures of dead end filter cartridges have utilized the high surface areas of particulates that can bind with and insolubilize enzymes. These efforts have utilized insolubilized particulates contained within a filtering layer itself and single pass operations. Canadian Patent No. 1,179,283 discloses a cartridge filter in which silica gel is embedded within a poly(vinyl chloride) membrane. An enzyme, insolubilized by adsorption onto the silica gel, was employed to isomerize sucrose to isomaltose. Similarly, U.S. Pat. No. 4,857,461 discloses a single pass, continuous process in which a dead end cartridge filter was utilized which contained, again within a web matrix, a crosslinked cellulose cation exchange resin possessing sulfonic acid groups. Enzymes were adsorbed via ion exchange, post crosslinked with glutaraldehyde, and utilized to isomerize sucrose in 97% yield with single pass flow rates up to about 12 mL/minute (flux rate=0.005 cm/minute). "Pressure driven enzyme membrane reactors" with flux rates as high as 0.20 cm/minute are more fully described by Schmidt-Kastner, et al., *Biochem. Eng.* [*Intl. Congr.*], 1986 (publ. 1987), 111–131 in which enzyme supported silica particulates are embedded within the porous structure of a membrane.

SUMMARY OF THE INVENTION

Briefly, this invention relates to a filter element comprising a composite filtration medium, the composite filtration medium comprising a filtration layer on the upstream surface of which are located insoluble enzyme particulates.

In another aspect, there is provided a filter cartridge including the above-described filter element.

In yet another aspect, there is provided a catalyst filter assembly comprising the filter cartridge and a cartridge filter housing, the composite filtration medium of the invention being capable of chemical conversion utilizing the insoluble enzyme particulates as catalyst.

In a further aspect, this invention relates to a method of chemical conversion comprising the steps of:

a) providing the filter element of the invention, and b) allowing a moving reaction solution to impinge upon the upstream surface of the composite filtration medium of the filter element for a time sufficient to effect chemical conversion, the filter element comprising insoluble enzyme particulates as catalyst.

In yet a further aspect, there is provided a method comprising the steps of:

a) providing a mixture comprising insoluble porous particulates and a solution comprising an enzyme (which can be an abzyme), the particulates and the enzyme having complementary reactive or attractive functionalities, b) allowing the solution comprising the enzyme to interact with the particulates for a time sufficient for the enzyme to become at least one of chemically or physically bound to the particulates, and c) wet-packing the particulates on the upstream surface of at least one filtration layer to provide a composite filtration medium.

In a still further aspect, there is provided a method for providing a composite filtration medium comprising the steps:

a) providing a filtration layer, and providing a solution comprising an enzyme and a crosslinkable polymer, b) crosslinking the polymer in the solution so as to provide crosslinked porous polymer particulates having the enzyme entrapped therein, and c) wet-packing the crosslinked porous polymer particulates having enzyme entrapped therein on the upstream surface of a filtration layer to provide a composite filtration medium.

In yet a further aspect, there is provided a method of providing a composite filtration medium comprising the steps:

a) providing a filtration layer, and providing insoluble enzyme particulates such as solid enzymes insoluble in nonaqueous liquids, crosslinked enzyme crystals, or whole cells, and b) wet-packing the enzyme particulates on the upstream surface of the filtration layer to provide a composite filtration medium.

The novel insolubilized enzyme filter elements are prepared by a novel process in which a slurry of insolubilized enzyme particulates in a liquid is passed through a filter cartridge comprising a filtration layer arranged in a dead end configuration and contained in a suitable housing so as to partially load a porous material (filtration layer) with enzyme particulates. Having thus prepared the filter element of the reaction system, a solution comprising a dissolved reactant is passed, preferably repeatedly and at relatively high velocity, through the filter element until the desired conversion to product is achieved. Since the filter element is only partially loaded with particulates, passage of reactant solution can be and is desirably conducted at relatively high flux rates with minimal pressure drop across the filter. Deactivation of the insolubilized enzyme due to the effects of pH is minimal because 1) correcting base or acid can be added elsewhere in the reaction system where efficient mixing can occur before re-exposure to the enzyme catalyst, and 2) single pass conversions are relatively low at high flux rates, thereby creating smaller pH changes to be corrected. Operation at high flux rates has also been determined to have a beneficial effect on reaction rate.

In this application:

"filtration layer" means a sheet-like woven or nonwoven porous material which can comprise one or more individual layers which can be combined to provide a single sheet; the average pore size is greater than 1 micrometer and up to 50 micrometers;

"composite filtration medium" means a filtration layer comprising enzyme particulates located on the upstream surface thereof; the medium has a flux rate of at least 0.01 cm/min at a filter cartridge pressure of at most 0.25 MegaPascals (MPa);

"filter element" or "filtering element" or "filtration element" means a composite filtration medium configured for fluid passage; it is the actual component of a catalyst filter assembly which accomplishes the filtering and/or reacting operation;

"filter cartridge" means a filtering device which is generally cylindrical;

"filter cartridge housing" means a support for a filter cartridge;

"catalyst filter assembly" means a filter cartridge in a housing;

"reaction system" means a catalyst filter assembly comprising at least a reaction solution contained in a reservoir, a pump, and associated tubing;

"flux rate" means the velocity of a liquid stream passing through a filtering element and is equal to flow rate divided by the frontal surface area of the filtering element. Described in this way, flow of a liquid stream can be characterized and is independent of the size of the filtering element; flux rate also contributes to pressure drop across a filter, i.e., increased flux rates generally mean increased system pressures. In commercial filter cartridge applications, it is highly desirable to provide a filter of minimum size which will process a maximum amount of liquid stream. Therefore, it is desirable that flux rate be increased by increasing the flow rate;

"insolubilized enzyme particulates" or "insoluble enzyme particulates" mean the insoluble particulates which are 1) products of reaction of soluble enzyme molecules (including artificial enzyme or abzymes) with insoluble particulates, i.e., covalent attachment, or the binding interaction of soluble enzymes with insoluble particulates, i.e., ionic and hydrophobic binding; 2) the insoluble particulates products resulting from the physical entrapment or encapsulation of an enzyme when a co-solute polymer has been rendered insoluble; 3) the solid enzyme particulates, insoluble in nonaqueous liquids and packed and reacted in those liquids, 4) those particulates when utilized in aqueous media, which are products of soluble enzymes that have been rendered crystalline and insoluble by chemical crosslinking; and 5) insoluble particulates, living or dead, animal, microbial, or plant cells which can comprise intracellular enzymes;

"insoluble" means not more than 1 part particulates dissolves in 100 parts of solvent at 23° C.; and "filter cartridge pressure" means the difference between inlet, or upstream, and outlet, or downstream, pressures across the filter cartridge unit in the reaction system.

The present invention filter elements overcome problems in prior art catalytic filters. Aside from the general problem of pH control with single pass operations that can be important for enzyme stability in common enzyme catalyzed reactions such as hydrolyses, prior art filters containing particulates within the filtering element present manufacturing challenges and offer only limited capacities. The hazards of air borne particulates are well known and manufacturing problems could easily arise in the construction of the filter cartridges by having to physically handle very small, reactive particulates which are required to be entrapped within a filter element. Prior art systems are also capacity limited in that more particulates must be loaded into the filtering element in order to increase catalyst capacity. Higher loading of particulates gives rise to a filtering element with reduced porosity, and operating system pressures would increase.

The present invention overcomes these problems of prior art filters by reducing contact of enzyme particulates and pH correcting fluids, avoiding handling of dry particulates, and providing high loading capacity of particulates at relatively low filter cartridge pressures.

DESCRIPTION OF THE INVENTION

Figure 1:
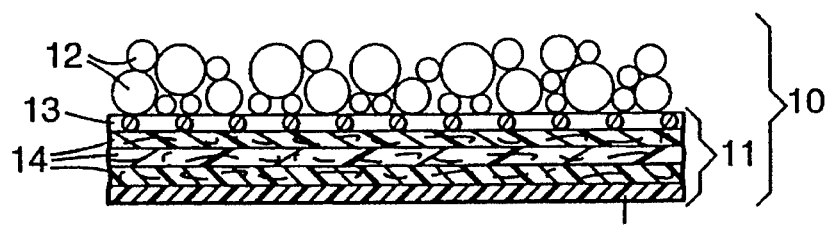
FIG. 1 is a schematic illustration of a cross-section of a composite filtration medium 10 comprising a preferred porous nonwoven web as surface filtration layer 11 which can be one or more individual layers, upon the upstream surface of which are located insolubilized enzyme particulates 12. The nonwoven filtration layer 11 which possesses well-defined pores can comprise coarse upstream prefilter layer 13, filtration layers 14 comprising a multiplicity of nonwoven filtration layers having increasingly finer downstream porosity, and a downstream nonwoven cover layer 15.
Figure 2:
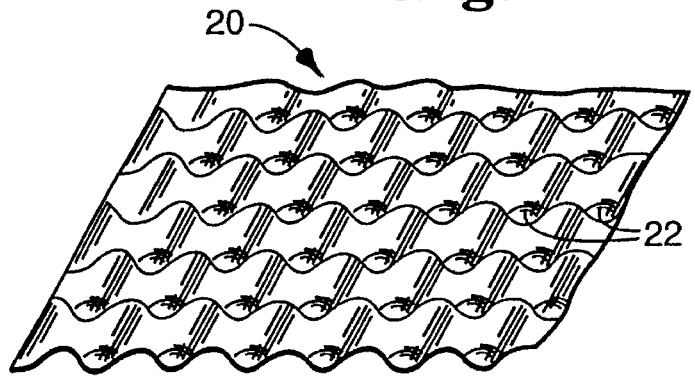
FIG. 2 is an illustration of a perspective view of a nonpleated portion of a pattern of embossed shapes 22 on composite filtration medium 20 utilized to produce filter cartridges. Embossing is conducted to increase frontal surface area and more completely define the surface filtering element. The insolubilized enzyme particulates are omitted from the illustration for clarity.
Figure 3:
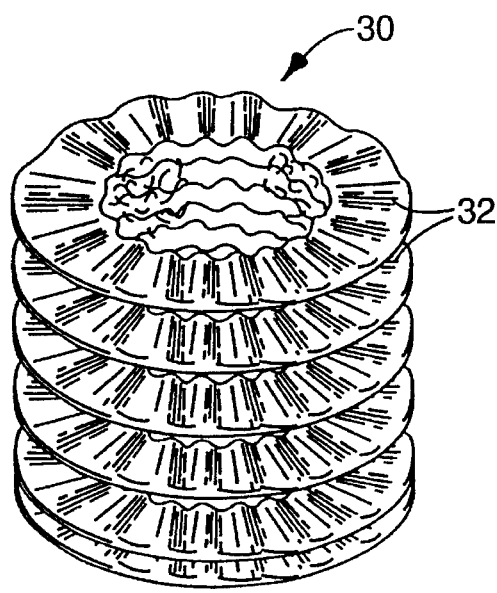
FIG. 3 is a perspective view of a longitudinally extended cylindrically pleated filter element 30; radial pleats 32 of preferred compound radially pleated filtration element 30 of the invention are shown; again, insolubilized enzyme particulates are omitted for clarity.
Figure 4:
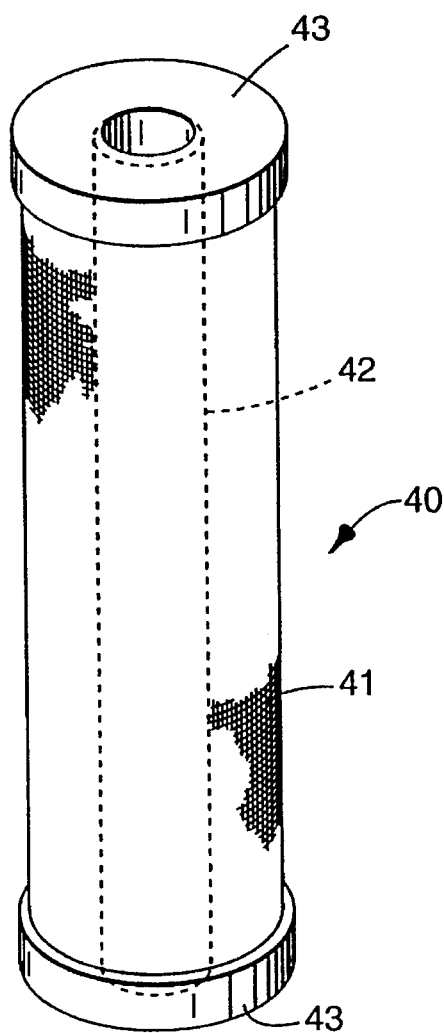
FIG. 4 is a perspective view which illustrates inner and outer supplemental support members for cylindrical filter cartridge 40. External support 41 such as a scrim or screen with a multiplicity of holes can provide additional support in an inward-out fluid flow mode to reduce the likelihood of rupturing the filter element. Similarly, inner support structure 42 consisting of a scrim or screen, a porous casing or similar construction can provide support to prevent the filter element (not shown) from collapsing under high pressure applications in a preferred outward-in fluid flow situation. In both cases, the supplemental support structures are normally attached to endpieces 43 of the filter cartridge to provide an integral unit.
Figure 5:
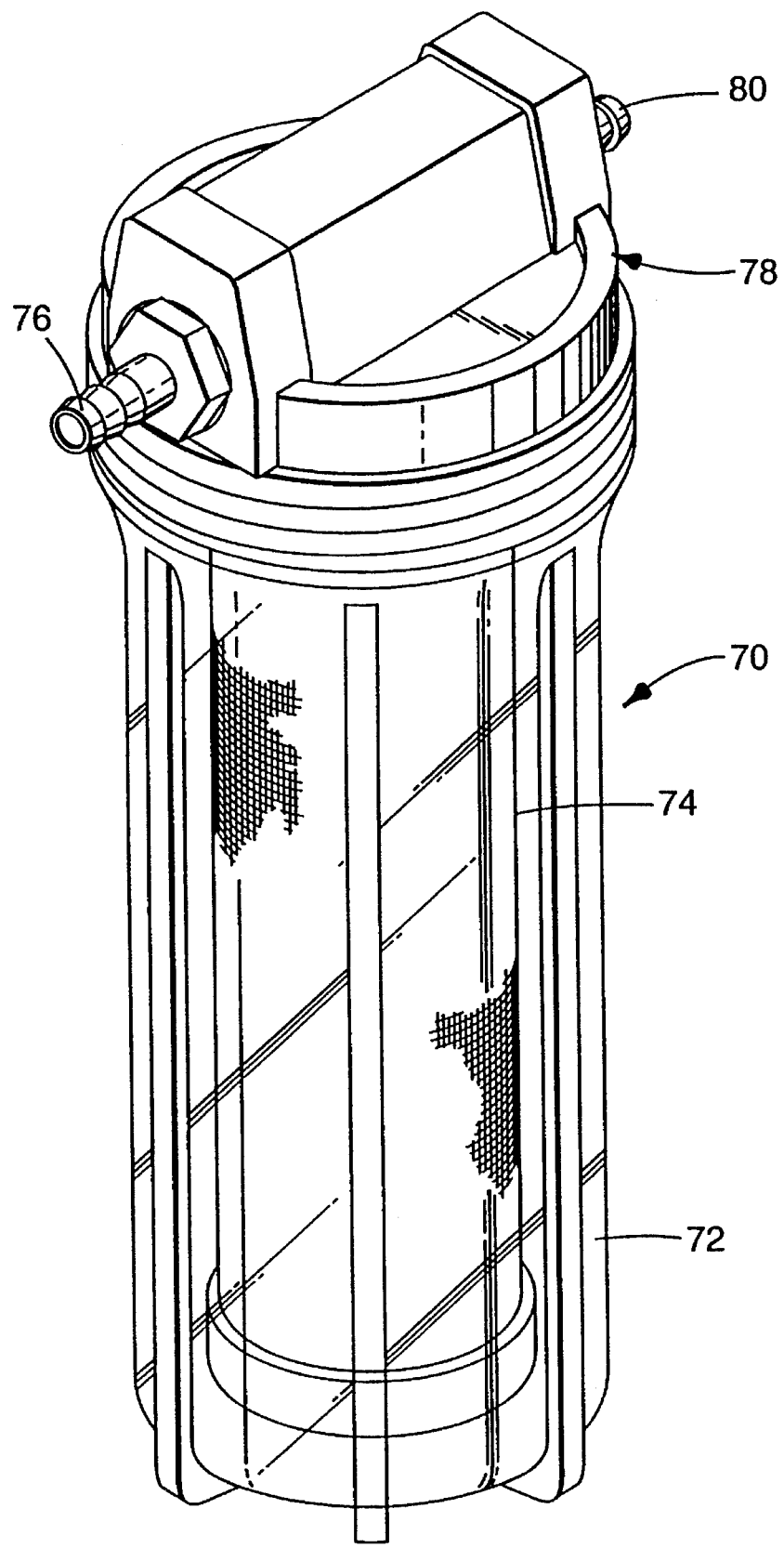
FIG. 5 is a perspective view of a catalyst filter assembly 70 of the invention. Filter housing 72 supports filter cartridge 74. Inlet port 76 of lid 78 allows slurry or solution to enter filter cartridge 74 in the preferred outward-in mode. The liquid exits catalyst filter assembly 70 through outlet port 80.

This invention provides a filter element of a catalyst filter assembly which utilizes an enzyme catalyst. Specifically, the novel component is the actual composite filtration medium in which reactant is converted to product by the enzyme catalyst. The catalyst filter assembly comprises a liquid filter cartridge which comprises insoluble enzyme particulates located on the upstream surface of the filtration layer of the filter element thereof and a suitable cartridge housing for the filter element connected to a reservoir of reaction solution. The filter cartridge is connected by suitable tubing to a pump capable of passing the reaction solution through the filter element and back into the reservoir so that the resultant solution can be repeatedly cycled through the filter element for further conversion of reactant to product, the passage being conducted with a flux rate of at least 0.01 cm/minute, preferably at least 0.1 cm/minute, and more preferably at least 0.3 cm/minute at a filter cartridge pressure of at most 0.25 MPa.

In the prior art, removal of particulates by filtration of liquid streams has been accomplished by applying one or a combination of the following filtration mechanisms, and liquid filter cartridges are presently commercially available that operate by each mechanism. The present invention utilizes a modification of these filter cartridges whereby the filtration layers retain an enzyme catalyst in a flowing reaction system.

i) Depth Filtration—This procedure is one in which a particulate-containing liquid stream is confronted by a filtration layer possessing a distribution of sized holes or pores and offers the particulates a rather tortuous pathway through the filtration layer. In the prior art, particulates were chiefly removed by adsorption and/or entrapment within the filtration layer itself. Depth filtration, often the coarse or first filtration procedure applied to a system and one designed to remove particulates from hundreds of micrometers (in diameter, largest dimension) to about 1 micrometer, suffers from problems of incomplete removal of particulates due to ill-defined pore sizes and steady, rapidly increasing system pressures as the filter becomes loaded.

ii) Surface (Cake) Filtration—This operation is preferred with the present invention and often follows depth filtration in the treatment of a liquid stream. In the prior art, it was conducted using multiple layers of glass or polymeric microfibers which possessed well-defined pore sizes, and the particulates generally did not penetrate within the filtration layer but remained trapped on the upstream surface of the layer. Particulate sizes down to about 1.0 micrometer were collected with efficiencies as high as 99.99%. High flux rates are readily achievable, and high capacities of particulates could be removed with relatively low system pressures until the filter is nearly full. In the present invention, it is advantageous to remove or realign the filtered particles on the surface of the filtration layer by multiple reverses of the liquid flow; this opportunity does not exist with prior art depth filters.

iii) Membrane (Screen or Sieving) Filtration— This filtering mechanism is very similar to surface filtration, except that precisely defined, very small pores are present which are capable of removing virtually all particulates with sizes as low as 0.05 micrometers. While providing "absolute" control of particulates remaining in the stream, problems of high system pressures, low capacity, and clogging also attend this filtration mechanism.

Useful surface filter cartridges in the present invention include the standard vertical pleated filters of U.S. Pat. No. 3,058,594 and, especially preferred, the horizontal, compound radially pleated filters of U.S. Pat. No. 4,842,739, all incorporated herein by reference as useful particle loadable filter cartridges for the present invention. A horizontal arrangement of pleats is preferred in the present invention because the cartridge filters are generally utilized in a vertical arrangement, and a greater percentage of particles is retained within the horizontal pleats when flow is discontinued and the cartridge stored between uses. Other filter cartridges such as string wound, resin bonded, and spray spun depth filters may also be utilized but generally lack the ability to load as much particulates as the surface filters while at the same time maintaining relatively low filter cartridge pressures.

Standard cylindrical, pleated filter cartridges are available, along with associated filter housings, from Ametek Inc. (Sheboygan, Wis.) in a variety of sizes, e.g., 4.8×24.8 cm (diameter×height), 6.7×24.8 cm, 6.7×50.8 cm, 11.4×24.8 cm, and 11.4×50.8 cm, filter element materials, e.g., cellulose, cellulose-polyester, glass-cellulose, polyester, polyolefin such as polypropylene, and ceramic, and average nominal pore sizes, e.g., 1, 2, 3, 5, 10, 20, 30, and 50 micrometers. Preferred cylindrical, compound radially pleated surface filter cartridges of all-polypropylene construction can be purchased from 3M Filtration Products (St. Paul, Minn.), with associated filter housings, in a variety of sizes, e.g., 7.6×25.4 cm, 7.6×50.8 cm, 7.6×76.2 cm, and 17.8×101.6 cm, and possessing average nominal pore sizes of 2, 5, 10, and 20 micrometers. Smaller disposable capsule filters and housings that are useful for smaller scale reactions are available from Gelman Sciences, Inc. (Ann Arbor, Mich.) in a variety of sizes, e.g., 6.3×6.4 cm, 5.8×17 cm, and 8.6×14 cm, filter element materials, e.g., polyamide such as acrylic coated polyamide and polypropylene, and average nominal pore sizes, e.g., 1, 3, and 5 micrometers.

Preferably, the composite filtration medium of the present invention comprises one or more nonwoven layers on the upstream surface of which are randomly disposed insoluble enzyme particulates. From a mechanical viewpoint, the composition of the actual nonwoven layer, which can be a fibrous web or a porous layer, is not critical when conducting reactions in aqueous media, providing it is not dissolved by or reacted with the reaction solution. All of the above-specified filtration layers generally perform well in water. It is only when reactions are conducted in organic solvents (or when the concentration of the organic reactant is very high and, as a result, the solution is relatively "organic") that special attention to the nature of the filtration layer is required. A preferred material because of its availability, cost, and chemical inertness to most organic solvents (and reactants and products) is polypropylene.

Selection of the pore size of the filtration layer depends directly on the size range of the insolubilized enzyme particulates to be retained on the upstream surface thereof and generally corresponds with the smallest particulates size. It has been determined, however, that even if a portion of the particulates possesses sizes smaller than the pore size of the filtration layer useful composite filtration media can be obtained. Because of the novel method of preparing the partially loaded composite filtration media vide infra these smaller particulates may pass through the filter element in early cycles; in later cycles, as a bed of particulates accumulates the device takes on the nature of a depth filter, and these smaller particles can also be retained and utilized in the invention. In the interests of time efficiency and utilizing the cartridge filter in the preferred surface filtration mode, however, it is preferred to utilize a surface cartridge filtration unit wherein at least 95% of the insolubilized enzyme particulates are removed in the first pass through the filter. Filtration layers with average pore sizes less than 1.0 micrometer such as porous, nonfibrous membranes are not preferred because they are susceptible to plugging, not only from adventitious particles that may be present but even by suspended reactants/products that are often encountered in highly concentrated reaction solutions. Generally a filter cartridge rated nominally at an average of 1–10 micrometers meets these criteria and provides an efficient filter element for the particulates utilized in the invention and also is capable of delivering relatively high flux rates at low filter cartridge pressures.

Enzymes useful in the invention include all classes of enzymes that have been employed for synthetic purposes, either by themselves, with appropriate cofactors, or with other enzymes in multienzyme processes. Examples of enzymes that have been utilized for synthetic purposes include but are not limited to alkaline phosphatase, cellulase, catalase, lysozyme, urease, papain, trypsin, chymotrypsin, subtilisin, thermolysin, horse radish peroxidase, xanthine oxidase, glucose oxidase, horse liver alcohol dehydrogenase, invertase, ficin, bromelin, pepsin, heparinase, sulfatase, sucrose synthetase, aldolase, aspartase, fumarase, beta-galactosidase, porcine pancreatic lipase, Rhizopus lipase, *Aspergillus niger* lipase, *Candida cylindraceae* lipase, *Mucor mihei* lipase, *Pseudomonas fluorescens* lipase, pig liver esterase, penicillin acylase, and horse liver esterase.

Insolubilized enzyme particulates useful in the invention are of five general types: 1) those resulting from covalent, hydrophobic, or ionic attachment to insoluble particulates; 2) those resulting from encapsulation or entrapment within an insoluble polymer matrix; 3) solid enzyme particulates insoluble in nonaqueous liquids and packed and reacted in those liquids; 4) crosslinked enzyme crystal particulates; 5) insoluble abzyme particulates; and 6) whole cells containing enzymes. The sizes of the insoluble enzyme particulates useful in the invention can range from a distribution in which a small portion, e.g., less than 5%, are submicrometer (largest diameter) to as large as several millimeters in largest diameter depending on the nature of the filter cartridge employed. Discussion and caveats relating to the lower size limit of particulates have already been given in relation to selection of a proper pore size filtering layer. The upper size limit of the particulates will depend on the particular kind of filter cartridge and is ultimately determined by the separation of pleat or fold tips. Particulate sizes are required to be less than the distance between pleat or fold inlet tips so that penetration within and on the upstream surface of the pleats or folds of the filtering element can occur. As a matter of working practicality, experience has shown that in order to prevent particles from acting in concert and exceeding the pleat/fold tip distance, a significantly smaller particle size, i.e., approximately ⅕ or less of the pleat/fold tip distance, preferably is utilized. An important attribute of the present invention is that relatively high concentrations of enzymes can be insolubilized by utilizing a particulate support possessing a relatively high surface area. Generally, for insolubilized enzyme particulate types which require a preformed insoluble support, the surface area should be at least 10 $m^2/g$, preferably at least 50 $m^2/g$, and more preferably at least 100 $m^2/g$. In order to provide these surface areas corresponding particle sizes preferably are in the range of submicrometer to 400 micrometers, more preferably 1–200 micrometers, and most preferably 10–100 micrometers in diameter.

Enzymes derive much of their water solubility from charged groups present on certain amino acid residues which are located at the periphery of the protein's three dimensional or tertiary globular structure. Covalent binding techniques are preferred in the present invention because these more peripherally located charged groups, especially amine groups on lysine residues, are often directly involved in the binding process, and, as a consequence, the active sites or catalytic centers are usually relatively unaffected and catalytic function is maintained. Also, with an efficient covalent binding process, desorption and leaching of the enzyme should not occur. Enzyme insolubilization by covalent attachment has been accomplished using a variety of insoluble particulate reactants typically possessing electrophilic functional groups such as azlactone, oxirane, chloromethylphenyl, cyanate, sulfonyl halide, carbonyl imidazole, carboxylic acids activated with carbodiimides, azide, aldehyde, thiolsulfonate, isothiocyanate, isocyanate, N-hydroxysuccinimide, tresyl ester, fluoronitroaromatics, vinyl sulfone, carboxylic anhydride, haloacetyl, and chlorocarbonate. These groups react with nucleophilic groups present on enzymes such as primary amine groups (e.g., lysine residues and protein termini), thiol groups (e.g., cysteine residues), and carboxylic acids (e.g., glutamic and aspartic acid residues). Commercially-available functional particulates supports useful for covalent binding of enzymes include: azlactone-functional EMPHAZE™ biosupport media (available from 3M Bioapplications, St. Paul, Minn.), oxirane-functional EUPERGIT™ supports (available from Rohm-Pharma, Darmstadt, Germany), chloromethylphenyl-functional Merrifield Resin supports (available from Aldrich Chemical Co., Milwaukee, Wis.), aldehyde-functional Actigel A™ supports (available from Sterogene Bioseparations Inc., Arcadia, Calif.), cyanate-functional Sepharose™ supports (available from Pharmacia, Uppsala, Sweden), carbonyl imidazole-functional Reacti-Gel™ supports (available from Pierce Chemical Co., Rockford, Ill.), vinyl sulfone-functional Immobilon™ supports (available from Millipore, Bedford, Mass.), and tresyl activated Sepharose™ supports (Pharmacia). Enzyme binding instructions are unique for each support and can be obtained from the manufacturer.

Charged groups on the outer surface of globular, water soluble enzymes can also be utilized for binding through exchange of free counter ions or gegenions on an insoluble particulate with like charged groups on an enzyme. As long as the ion exchanged product does not encounter other ions that would displace the enzyme gegenion, the bond can endure. Disadvantages of this method of non-covalent binding include: 1) the susceptibility of the bond to cleavage caused by changes in pH and ionic strength as reaction takes place and 2) the highly charged microenvironment of the enzyme in the bound condition is quite different from its normal environment in aqueous solution and can lead to alterations in necessary association of protein components, i.e., quaternary structure, of a working enzyme and deterioration in catalytic function. Insoluble particulates possessing nucleophilic functional groups such as amine groups which are normally protonated and charged at binding pHs are also available, e.g., DEAE Sepharose™ supports (Pharmacia), with instructions for protein binding.

Despite the presence of water solubilizing amino acid residues on an enzyme's outer surface, the majority of amino acids that comprise most enzymes are relatively hydrophobic in nature because of the presence of a variety of hydrophobic aromatic and aliphatic groups. This hydrophobic nature of the more centrally located amino acids of globular enzymes has been utilized to hydrophobically bind enzymes to relatively hydrophobic particulates supports such as n-octyl Sepharose supports, palmityl Sepharose supports, beta-naphthyl cotton, celite, hexadecyl silica, oil-impregnated polypropylene, and others. In certain instances the strength of the hydrophobic interaction alone is sufficient for use as insolubilized enzyme particulates in the present invention. An added protection against reversal of the hydrophobic binding process is to treat the enzyme particulates with a crosslinking agent for the enzyme such as glutaraldehyde which will provide additional stabilization against loss or leaching of the enzyme from the support particulates. A disadvantage with non-covalent binding techniques such as hydrophobic binding is that the binding interaction tends to involve the enzyme quite deeply within its globular structure such that the active catalytic centers are often affected, and catalytic function will continue to diminish with time as the binding process proceeds.

With the above types of insolubilized enzyme particulates, immobilization or insolubilization can occur by conventional treatment of the insoluble reactive particulates in a batchwise fashion with the enzyme contained in a suitable solvent. Alternatively, the insoluble reactive particulates can first be loaded onto the filter cartridge, and the enzyme immobilized subsequently by recycling a solution of the enzyme through the particle-loaded cartridge filter. This latter method of insolubilizing the enzyme offers considerable potential to significantly reduce manufacturing costs and environmental concerns because synthesized particulates need not be isolated, dried, sized, etc., but can be directly loaded onto a filter cartridge from the polymerization or synthesis reactor.

Insolubilized enzyme particulates of the invention can also be prepared by employing entrapment or encapsulation methods with soluble enzyme, cellular organelle, or whole cell components. In general, to maximize enzyme entrapment and minimize leakage, a high degree of crosslinking is required which can limit diffusion of reactants and products. Also, the active sites of enzymes tend to be somewhat encumbered by the entrapping medium and inaccessible to high molecular weight reactants. Methods have been derived for enzyme entrapment within polyacrylamide/methylene-bis-acrylamide networks, alginate gels, and fiber forming polymers such as cellulose triacetate. Microencapsulation within semipermeable membranes, liposomes, and hollow fibers has also been utilized to insolubilize enzymes. In addition, various pre-polymer techniques have been employed including: photocrosslinking systems and isocyanate-functional resins which can crosslink and encapsulate aqueous solutions or suspensions of biocatalysts.

Many enzymes are solids, some crystalline, when water is removed from them. These solid enzyme preparations are generally insoluble in non-aqueous solvents and can be loaded directly onto filter elements, especially with packing liquids and reaction solvents such as hexane, heptane, toluene, and xylene. These insoluble enzyme particulates may be desirable because non-aqueous solvents, while poor solvents for the solid enzymes, tend to be excellent solvents for reactants and products.

Another kind of insolubilized enzyme particulates that is useful in the invention is the "Cross-Linked Enzyme Crystals" (CLECs) commercialized by Altus Biologics (Cambridge, Mass.). In the CLEC™-forming process, an enzyme is first crystallized by a variety of techniques and then permanently insolubilized by treatment with a crosslinking agent such as glutaraldehyde. The resulting CLECs can be utilized directly as the insolubilized enzyme particulates of the invention.

One further kind of insolubilized enzyme particulates is the covalently immobilized artificial enzyme known as a catalytic antibody or abzyme. These are catalysts in which an antibody present in a living organism is treated with an antigen that structurally resembles the transition state of another substrate for which the catalyst is being designed. For example, normally tetracoordinate phosphonates have been used as antigens for the production of antibodies (abzymes) that can be used to stereospecifically hydrolyze carboxylic esters which have tetracoordinate transition states. These abzymes have been immobilized onto inorganic particulates materials by procedures disclosed by K. D. Janda, et al., *J. Am. Chem. Soc.*, 1990, 112, 8886, which is incorporated herein by reference.

Useful microorganisms or whole cells that have been harvested and employed synthetically include *Penicillium digitatum, Rhizopus nigricans, Mucor rouxianus, Candida utilis,* Saccharomyces species, *Pichia membranaefaciens, Rhodosporidium toruloides, Pseudomonas putida, Phanerochaete chrysoporium, Hansenula anomala, Rhodotorula rubra, Kloeckera saturnus, Nocardia salmonicor, Proteous vulgaris, Lactobacillus kefir, Sulfolobus sulfataricus, Geotrichum candidum,* and *Torulaspora delbrueckii.*

Having thus described the filter cartridges, reaction systems, and insoluble enzyme particulates, the novel process by which the catalyst filter assemblies are prepared will now be detailed. The process involves the steps of:

i) attaching in a closed loop arrangement the filter cartridge contained in a housing to a pump capable of delivering a flux rate of at least 0.01 cm/minute and to a reservoir containing a slurry of the insoluble enzyme particulates in a liquid;

ii) pumping the slurry through the filter cartridge in a recycling mode until the desired amount of insolubilized enzyme particulates has been loaded or until the filter cartridge pressure reaches about 0.15 MPa.

Pumps useful in the invention provide flux rates through the filter cartridge in excess of 0.01 cm/minute, preferably in excess of 0.10 cm/minute, and more preferably in excess of 0.30 cm/minute. The pumps and associated gasketing and tubing/piping through which the reaction solution flows preferably are relatively unaffected by the reaction solution and small changes in pH. Preferred pumps include peristaltic, diaphragm, gear, and centrifugally driven pumps in which the actual pump components contacting the reaction solution are constructed of stainless steel or polytetrafluoroethylene (PTFE). Most types of rubber or plastic tubing/piping are suitable for reactions conducted in aqueous media, but for use in organic solutions (and when high organic reactant concentrations are employed even with a water solvent) polypropylene, polyethylene, PTFE, stainless steel, and glass tubing should be employed. Preferred gasketing materials to interface the connection of filter cartridges to filter housings and with the rest of the system include PTFE and polypropylene.

In contrast to "dry" packing manufacturing techniques, "wet" packing the particulates onto the filtration layer by use of a liquid carrier assures that the particulates are located in regions of the filtering element which are later accessible to reaction solutions. The particulates are randomly located on the filtration layer in the sense that their positions are not pre-selected, although the flow of the liquid carrier may influence the ultimate location of particulates. In packing the filter cartridge by the above process it is desirable to employ fairly dilute concentrations of the particulates in the liquid, e.g., less than 5 weight percent of the liquid slurry, during each packing session in order to achieve relatively uniform partial loading of the filtering element. The particulates can be added to the reservoir in a portionwise fashion, with visual clarification of the reservoir contents occurring between each portion. The flux rate of the packing operation preferably is at least 0.01 cm/minute, more preferably at least 0.10 cm/minute, and most preferably at least 0.30 cm/minute. Relatively high flux rates are desirable especially with the preferred compound radially pleated filter cartridges so that the particulates can better permeate the folds of the pleated filter element, thus accessing more of the filter element and facilitating high loading. The liquid employed to slurry the particulates may or may not be the same liquid that will function as solvent for the reaction that will be subsequently conducted. Useful liquids include hexane, heptane, toluene, ethyl acetate, methanol, ethanol, t-butanol, acetonitrile, and water, preferably buffered water.

The particulates are loaded into the reservoir and ultimately onto the upstream surface of the filter element until the filter cartridge pressure reaches not more than 0.15 MPa, preferably not more than 0.10 MPa, and more preferably not more than 0.05 MPa. A practical filter cartridge pressure limit for a fully loaded preferred compound radially pleated filter cartridge is about 0.25 MPa. As a general rule of application of filter cartridges, when filter cartridge pressures in excess of about 0.05 MPa are attained, subsequent loading of additional particulates results in increasingly larger filter cartridge pressures. Especially with the lower recommended filter cartridge pressures, however, flux rates of solutions passing through the filter cartridges remain high and in the range desirable for the purposes of this invention. In this fashion, the unit can still respond to adventitious particulates that are likely to be encountered during subsequent reactions and handling operations. By reserving the remaining particulate capacity during operation, shut downs are averted and filter cartridge lifetimes can be extended.

The particulate loaded filter cartridge is now ready to be utilized as a catalyst filter assembly to catalyze a chemical reaction in a solution passed through. The catalyst filter assembly and cartridge are schematically illustrated in FIGS. 1–5.

After loading the particulates to provide the composite filtration media, the inlet and outlet tubing ends are removed from the reservoir (or left attached if the packing reservoir will also function as reactant solution reservoir) and are attached to an appropriate reaction vessel containing the reactant dissolved in a liquid solvent. Reactants can be any organic or inorganic solute that can be chemically transformed by an enzyme catalyst into a reaction product. Useful reactants which can be employed singly include various carbohydrate compounds that can be isomerized, such as glucose and sucrose, as well as squalene-like compounds that can be cyclized. Useful reactant pairs include esters-water, nitriles-water, amides-water, olefins-water, acids-alcohols, anhydrides-alcohols, anhydrides-amino acids, esters-amines, aldehydes-hydroxyketones, aldehydes-cyanohydrins, nitrile oxides-olefins, oxirane-water, and olefins-amines. Cofactor mediated reductions involving enzyme catalysts include ketone, aldehyde, and olefin substrates. Similarly, oxidations have involved alcohol, aldehyde, ketone, sulfide, and various aliphatic and aromatic hydrocarbon substrates.

The liquid solvent utilized depends largely on the nature of the reaction to be conducted. If water is a reactant, water is highly desirable to be used as solvent as well; if an esterification or transesterification is the desired reaction, the corresponding alcohol or ester may be used as solvent. A listing of liquids useful as solvents for the chemical reaction to be conducted would include those listed above for filter cartridge packing.

Additional additives such as buffering agents may also be required to maintain the insolubilized enzyme in a stable condition, especially when the chemical reaction creates acidic or basic products.

It is normally desired, of course, to obtain the greatest quantity of product in the shortest period of time. As is apparent to one skilled in the use of enzyme catalysts, the concentrations of enzyme and reactant and the extent to which product is allowed to accumulate have important influences on the reaction. In general, for a given reactant or substrate and in the absence of complicating substrate inhibition factors, a substrate concentration significantly, e.g., 10 times, greater than the so-called Michaelis-Menten constant (Km) is desired so that reaction will occur at maximum velocity.

The velocity with which a reaction solution is passed through the composite filtration medium, i.e., the flux rate, and recycled also has been determined to be an important criterion to performance in the present invention. An explanation of the effect of flux rates may involve better shear mixing of reactant with the insoluble enzyme particulates at higher flux rates, access to a greater number of particulates contained deep within pleats or folds of the filtering element at higher flux rates, and/or other factors. A flux rate of reaction solution passage of at least 0.01 cm/minute is preferred, more preferably at least 0.10 cm/minute, and most preferably at least 0.30 cm/minute.

Figure 6:
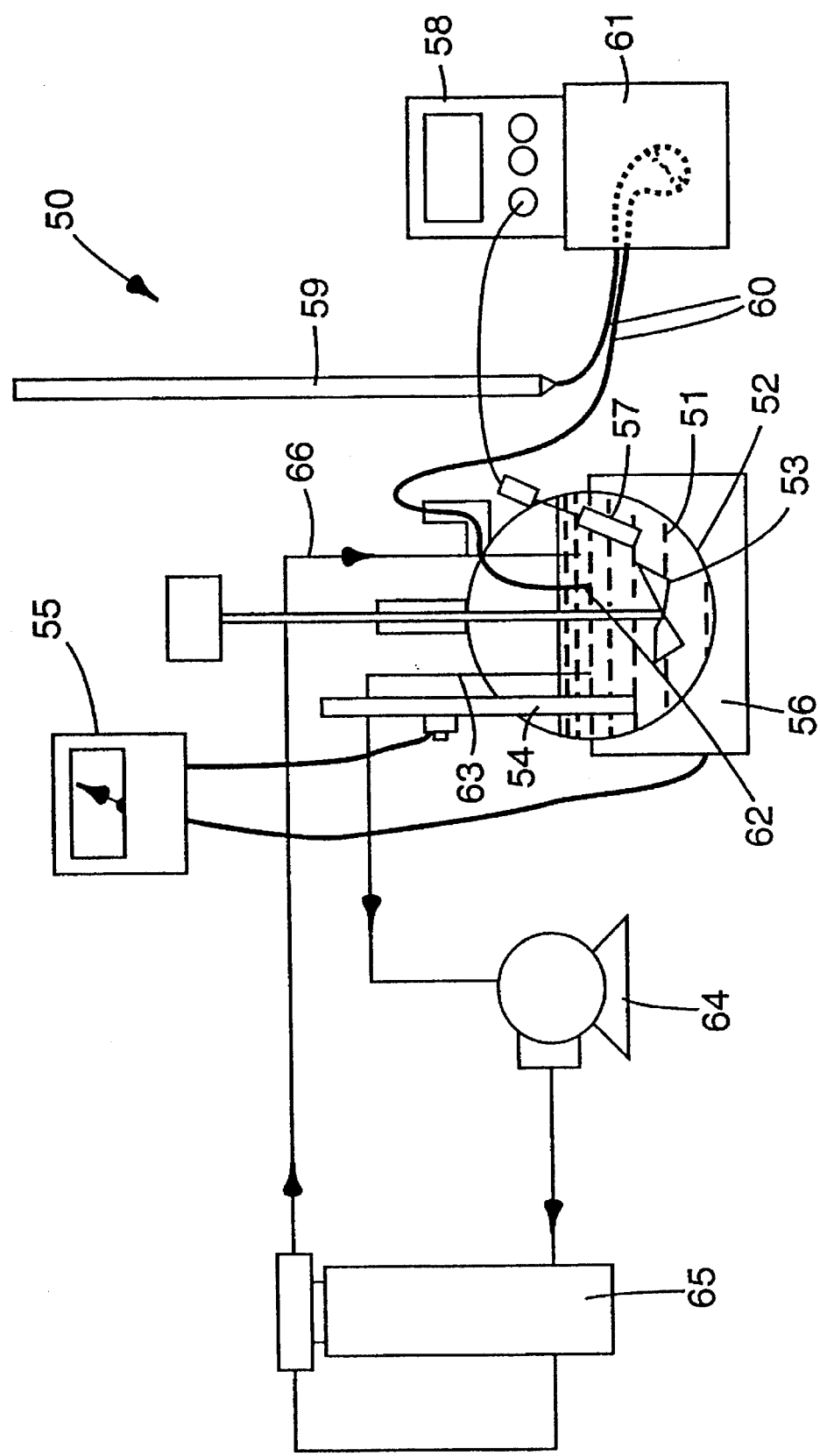
FIG. 6 is a schematic illustration of reaction system 50 of the invention. Reaction solution 51 is housed in vessel 52 which is equipped with stirring apparatus 53, thermometer 54 connected to temperature controller 55, also connected to device 56 for heating the solution, and pH electrode 57 connected to pH stat 58 further connected to pH correcting fluid (complementary to acidic or basic products of the reaction) contained in buret 59 still further connected via tubing 60 to pump 61 which can deliver a titrant to the reaction solution reservoir via inlet 62. Reaction solution 51 is pumped from outlet tube 63 by pump 64 through the catalyst filter assembly 65 and back into the reaction vessel via inlet tube 66 (arrows show direction of liquid flow).

An additional attribute of the present invention and one readily discerned by examination of the reaction system of FIG. 6 is that pH correcting titrant fluids in their full, undiluted strength do not have the opportunity to encounter the insolubilized enzyme particulates. In contrast to conventional batchwise utilization of an immobilized enzyme in which titrant is added directly to a reaction slurry, titrant in the present invention is added to the reaction solution reservoir where it can be stirred and diluted before encountering the insolubilized enzyme particulates contained on the cartridge filter and housed in another part of the modular reaction system. This is a very important feature of the present invention and one that contributes to the maintenance of initial, peak performance over the course of many reuses. The insolubilized enzyme particulates remain in their active catalytic form much longer than if they were applied in a slurry or batchwise fashion and were made to suffer the deleterious effects of temporary, but wide swings in pH.

The filter elements of the present invention finds utility in a variety of catalyzed chemical reactions, for example in esterifications, isomerizations, oxidations, reductions, and cyclizations.

Objects and advantages of this invention are further illustrated by the following examples, but the particular materials and amounts thereof recited in these examples, as well as other conditions and details, should not be construed to unduly limit this invention.

EXAMPLE 1

This example teaches the preparation of a filter element of the invention in which penicillin acylase was covalently immobilized on azlactone-functional EMPHAZE Biosupport Media and was loaded onto a preferred compound radially pleated cartridge filter.

Insolubilized Penicillin

Acylase Particulates

Penicillin acylase (PGA; penicillin amidohydrolase, ED 3.5.1.11) was purchased from Pharma Biotechnologie Hannover (Hannover, Germany) as a solution in 0.1M sodium phosphate, pH 7.5, with typical protein contents ranging from 60–70 mg/mL. Specific activities ranged from 17–24 Units/mg protein; one Unit is defined as the amount of enzyme required to cleave one micromole of phenylacetic acid from penicillin G per minute at 37° C. and pH 7.8, as determined by titrating the released acid with sodium hydroxide. The enzyme was used as received.

A particular sample of azlactone-functional EMPHAZE Biosupport Media (obtained from 3M Bioapplications, St. Paul, Minn.) was utilized in binding studies in which 80% of the particulates possessed sizes between 6 and 40 micrometers (mean=21 micrometers) with no particles being detected larger than 70 micrometers; particle sizes were determined using a Coulter LS-100 Particle Size Analyzer (Coulter Corp., Hialeah, Fla.). To 10.00 grams of the EMPHAZE material were added a PGA solution (399 mg PGA, 7200 Units) dissolved in 5.75 mL of 0.1M phosphate) and 600 mL of 1.0M sodium citrate, 0.05M disodium hydrogen phosphate, and 0.05M sodium dihydrogen phosphate solution. The slurry was tumbled at room temperature for 5 hours; the mixture was filtered and the filtercake was washed with phosphate buffered saline (0.85% sodium chloride and 0.10M sodium phosphate at pH 7.2) (2×600 mL), 0.005M EPPS (N-[2-hydroxyethyl] piperazine-N'-[3-propane-sulfonic acid]; pH=8.0; Sigma) (2×600 mL), and then the filtercake was resuspended in 600 mL of 0.01 M phosphate and 0.1M potassium chloride (pH=7.6). The activity of the insolubilized enzyme particulates was 6600 Units.

Loading the Insolubilized PGA Particulates onto a Cartridge Filter

For the loading procedure a Millipore Peristaltic Pump (802G230, Millipore Corp., Bedford, Mass.), an Ametek Water Filter Housing (Model PSCL, Ametek, Inc., Sheboygan, Wis.) containing a 3M High Capacity Liquid Filter Cartridge (Model 313B, 3M, St. Paul, Minn.; 7.6×25.4 cm; all-polypropylene; 2 micrometer pore size rating) connected with polypropylene gaskets, and 6 L beaker equipped with efficient magnetic stirring capability were interconnected by Norprene™ tubing (catalogue no. 6485-73; available from Cole-Parmer Instrument Co., Chicago, Ill.). Into the beaker reservoir were placed 5 L of 0.01 M potassium dihydrogen phosphate and 0.1M potassium chloride at pH 7.6. The pump was engaged at 3.7 L/minute flow rate (flux rate= 0.44 cm/minute); the inlet and outlet tubing ends were immersed beneath the surface of the liquid in the reservoir so that air bubbles would be less likely to form. Next, 100–150 mL portions of the above PGA particulates slurry were added, and the turbid mixture was stirred briskly and allowed to visually clarify between each slurry addition. A total time of about 20 minutes was required for the loading operation. This cartridge will be subsequently referred to as the "PGA cartridge". Between reactions the cartridge and its housing were stored at 5° C.

EXAMPLE 2

This example teaches the preparation of a filter element of the invention in which pig liver esterase covalently immobilized on an azlactone-functional dispersion polymer was loaded onto a compound radially pleated cartridge filter.

Preparation of the Azlactone-Functional Dispersion Polymer

A three-liter, three-necked round bottomed flask equipped with a mechanical stirrer, thermometer, gas inlet, dropping funnel, and condenser was charged with trimethylolpropane trimethacrylate (50.0 grams; available from Sartomer Co., Inc., Exton, Pa.), hydroxyethyl methacrylate (HEMA; 30.0 grams; available from Alcolac, Baltimore, Md.), 2-vinyl-4,4-dimethylazlactone (VDM; 20.0 grams; available from SNPE, Inc., Princeton, N.J.), 1.67 grams of a stabilizer solution [33% solids in Isopar G™; consisting of a lauryl methacrylate:VDM (94:6 w/w) copolymer reacted with HEMA], and heptane (800 mL). The solution was stirred (350 rpm) and sparged with nitrogen for 10 minutes before warming to 70° C. Azobis(isobutyronitrile) (2.5 grams; available from Polysciences, Inc., Warrington, Pa.) was added to the hot solution, and in a few minutes particles were visible in the reaction vessel. As the polymerization proceeded, eight 200 mL portions of deoxygenated heptane were added at various times to facilitate mixing. After 2 hours from the detection of particles, the reaction mixture, now a white creamy flocculent polymer mass, was allowed to cool. The solid was filtered and washed with heptane and ethyl acetate before drying to constant weight at less than 1 Torr. The polymer weighed 98.9grams (98.9% yield), possessed a surface area (BET method) of 93 $m^2/g$, a % nitrogen of 1.8% indicating VDM incorporation of 18%, and a particle diameter size range that showed while 80% of the particles possessed acceptable diameters between 14–203 micrometers (mean size=54 micrometers) some particle agglomerates were present with unacceptably large diameters approaching 1000 micrometers. In order to prevent filtering operations from becoming difficult, the larger agglomerated material will be broken up into smaller sizes after the enzyme binding procedure.

Insolubilized Pig Liver Esterase Particulates

Pig liver esterase (PLE; Carboxyl esterase, EC 3.1.1.1) was purchased from Sigma Chemical Co. (St. Louis, Mo.) as a suspension in 3.2M ammonium sulfate. Its specific activity was about 200 units per milligram protein (one unit is defined as the amount needed to hydrolyze one micromole of ethyl butyrate per minute at pH 8.0 at 25° C.). Before binding, the enzyme was first dialyzed against three changes of a solution consisting of 0.7M sodium citrate and 0.05M disodium hydrogen phosphate adjusted to pH 7.5. This procedure brought the enzyme to the desired pH and ionic strength and removed ammonium ions. The dialysate was then filtered through a 0.45 micrometer cellulosic syringe filter (model SLHA 02505, available from Millipore Corp., Bedford, Mass.), and the enzyme concentration determined spectrophotometrically using an extinction coefficient of 14.8 at 280 nm (1%, 1 cm). This was determined gravimetrically and is close to the value of 13.8 reported by Barker and Jencks in *Biochemistry*, 1969, 8, 3879–3889.

To 10.00 grams of the azlactone-functional dispersion polymer prepared above were added 30 mL of a PLE solution (264 mg PLE dissolved in the citrate/phosphate dialysate solvent), 600 mL of 0.7M sodium citrate and 0.1M phosphate (pH=7.4), and 0.60 grams of Pluronic L-31™ surfactant (available from BASF Corp., Parsippany, N.J.) dissolved in 15 mL of water. The mixture was shaken mechanically for about an hour, then tumbled gently an additional 2 hours at room temperature. The mixture was filtered (sintered glass funnel; 10–20 micrometer average nominal filter rating), and the filtrate possessed essentially background activity when examined as a catalyst for the hydrolysis of p-nitrophenyl acetate. The filtercake was washed with 400 mL portions of phosphate buffered saline and 0.005M EPPS (three times). The filtercake was then resuspended in 1% Pluronic L-31 surfactant dissolved in 0.005M EPPS (600 mL) and tumbled at room temperature for 16 hours. The mixture was filtered, and the filtercake was washed well with 400 mL portions of 0.005M EPPS. The filtercake was then suspended in 600 mL portions of 0.05M EPPS and homogenized using a Willems Polytron Model PT 10-35 Tissue Homogenizer (available from Brinkmann Instruments, Westbury, N.Y.) at medium speed for 5 minutes. The resulting particle size range showed no particles larger than 200 micrometers in diameter and an 80% range between 6 and 112 micrometers.

Loading the Insolubilized PLE Particulates onto the Cartridge Filter

The procedure of Example 1 was utilized with the above slurry being loaded over a 20 minute period using the reservoir containing 0.05M EPPS. The packing flow rate was 4 L/minute (flux rate=0.48 cm/minute); no free PLE was detected in the clarified reservoir after the loading operation. The cartridge will be designated "PLE cartridge" in subsequent examples.

EXAMPLE 3

This example teaches that surface filtration cartridge filters for purposes of this invention possessed superior loading capacities compared to depth filters. Also, the superiority of the compound radially pleated filters was demonstrated not only by superior loading capacity but also by providing the lowest flux rates of the filter cartridges evaluated at constant flow rate.

The loading procedure of Example 1 was utilized, except that pressure gauges were inserted on the inlet and outlet ports of the filter housing unit. Particulates utilized for all the cartridge filters described in Table I below were EMPHAZE Biosupport Media of Example 1, except no PGA was bound for this series of trials designed to measure particle loading capacity. The buffer solution was replaced by water, and the flow rate was 3.8 L/minute. Weighed portions of EMPHAZE were slurried in water, added to the reservoir, and the effective capacities were determined by noting the quantity of particulates added when the inlet pressure exceeded outlet pressure by 0.05 MPa. The data is given in Table I.

TABLE I

| Cartridge Filter (Supplier, Porosity, Construction) | Effective Capacity, Grams | Flux Rate (cm/min) |
|---|---|---|
| 3M (St. Paul, MN), average nominal pore size 2 micrometers, compound radially pleated polypropylene surface filter | 33.5 | 0.45 |
| Filterlite ™ (Timonium, MD), average nominal pore size 2 micrometers, vertically pleated cellulose surface filter | 18.9 | 0.91 |
| AMETEK (Sheboygan, WI), average nominal pore size 5 micrometers, resin bonded cellulose depth filter | 5.0 | 5.85 |
| Pall (East Hills, NY), average nominal pore size 1 micrometer, spun bonded polyester depth filter | 7.0 | 7.17 |
| Filterite, average nominal pore size 1 micrometer, string wound cellulose depth filter | 7.2 | 7.17 |
| Filterite, average nominal pore size 5 micrometers, string wound cellulose depth filter | 7.5 | 7.17 |

EXAMPLE 4

This example makes the following points: 1) the efficient synthetic utilization of the PGA cartridge was demonstrated; 2) the catalytic efficiency of the immobilized PGA was shown to be comparable to free, soluble PGA, i.e., the specific activity of the insolubilized enzyme was high; 3) there was no loss in catalytic activity by incorporating the immobilized PGA particles in a recycling flow system on the upstream surface of a filter element; and 4) the catalytic performance of the PGA cartridge remained essentially unchanged after many reuses.

The reaction system of FIG. 6 was utilized in which the reaction reservoir 52 was a 5 L round-bottomed flask, the pump and tubing were the same as in Example 1, the cartridge filter assembly 65 was the same as for the PGA cartridge of Example 1, the temperature controller 55 was a Therm-O-Watch™ (Model L7-800SS; available from Instruments for Research & Industry {Cheltenham, Pa.), the pH stat with titrant pump was a model pH 4000 (available from New Brunswick Scientific [Edison, N.J.]), the electrode 57 was an Ingold pH Electrode (Model 9100232, Wilmington, Mass.), and the 0.750M sodium hydroxide titrant was contained in a 100 mL buret 59.

Figure 7:
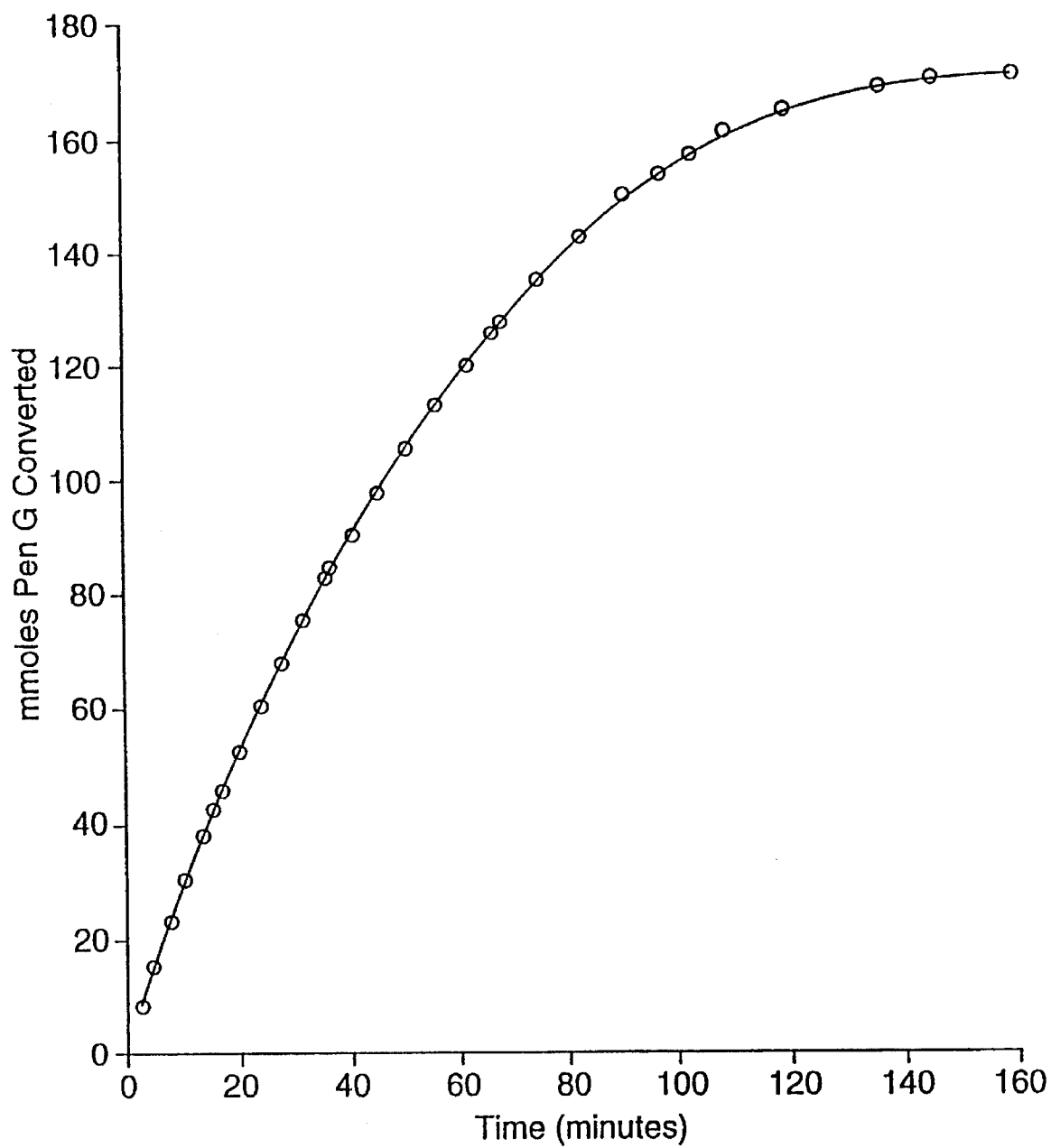
FIG. 7 is a graph showing the conversion of 168 mmoles of Penicillin G to 6-aminopenicillanic acid and phenylacetic acid versus time as conducted in Example 4.

A buffer/electrolyte solution (1320 mL) consisting of 0.01 M potassium dihydrogen phosphate and 0.1M sodium chloride at pH 7.8 was added to the reaction reservoir. With the 1280 mL already in the cartridge filter housing and associated tubing, the system volume at this point was 2600 mL. The pump was engaged at 4 L/minute and the buffer solution was circulated and warmed to 28° C. Penicillin G (60.0 grams; 0.168 mole; available from Sigma) was dissolved in 400 mL of the buffer/electrolyte solution and was added in one portion; the total system volume was 3000 mL. The pH was maintained at 7.8 by the pH stat by addition of caustic from the buret. The progress and actual rate of the reaction were monitored by observing the quantity of caustic added with time; a plot of Penicillin G converted (equal to the mmoles of caustic added to neutralize the phenylacetic acid by-product) versus time is shown in FIG. 7. The curve was initially linear, i.e., zero order, but the effects of product inhibition which are well-known for this reaction gradually slowed the rate as reaction proceeds, and the line deviated from linearity, with complete conversion being achieved in about 160 minutes.

It is instructive to understand whether the catalytic efficiency of PGA has been impuned during the insolubilization and when incorporated on the upstream surface of a cartridge filter. In order to determine the effects of these manipulations of PGA, the insolubilized PGA described in Example 1 was prepared again but utilized as a slurry added in a conventional batchwise fashion to the reaction to convert the same quantity of Penicillin G and in the same total system volume as above. A plot of mmoles of Penicillin G converted with time for the first approximately 25% reaction during which linear, zero order plots were obtained and reaction rates were directly compared is shown by line A of FIG. 8 (slope=rate=2.60 mmoles/minute).

The activity of PGA exhibited by the EMPHAZE particles was 6,600 Units. When 6,600 Units of soluble PGA were added to a 28° C. solution of Penicillin G in the same buffer solution, the quantity of Penicillin G converted versus time is shown by line B in FIG. 8 (rate=2.68 mmoles/minute). This result showed that immobilization produced no ill effects on the catalytic performance of the PGA, as very comparable performance was observed (as indicated by substantially identical slopes) with both free and insolubilized forms of PGA.

Figure 8:
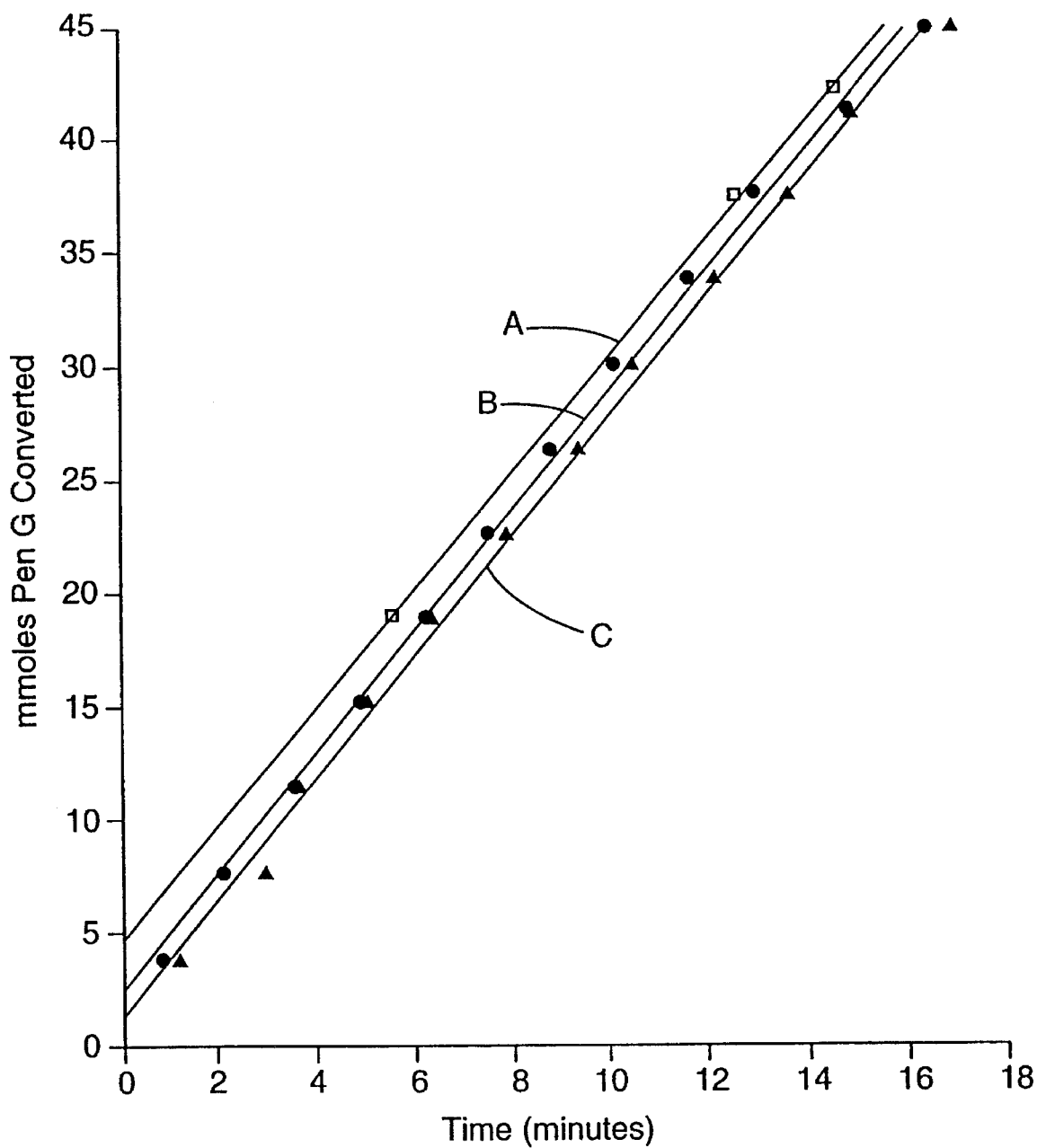
FIG. 8 is a graph showing the first 25% reaction of hydrolysis of Penicillin G versus time as conducted in Example 4. Line A was obtained with insolubilized PGA; line B with free PGA; and line C with insolubilized PGA within a cartridge filter.

To assess the effect of incorporation within the cartridge filter, the performance of the PGA cartridge was replotted in FIG. 8 (line C; rate=2.68 mmole/minute), and the result showed no loss in performance due to incorporation within the cartridge. Furthermore, when the reaction using the PGA cartridge had been rerun 19 times, the initial rate was still 2.68 mmoles/minute indicating excellent reusability and stability of the PGA cartridge. The reuse information also provides insight into how strongly the PGA was bound and how resistant covalently insolubilized enzymes were to leaching. Not only did the bound PGA have to withstand the rigors of reaction solution flow twenty times, but also 8–10 L of rinsing buffer solutions were employed between each use, all at 4 L/minute flow rate.

EXAMPLE 5

This example teaches that the PGA cartridge functioned better when the reaction solution flux rate was greater than 0.01 cm/minute.

Figure 9:
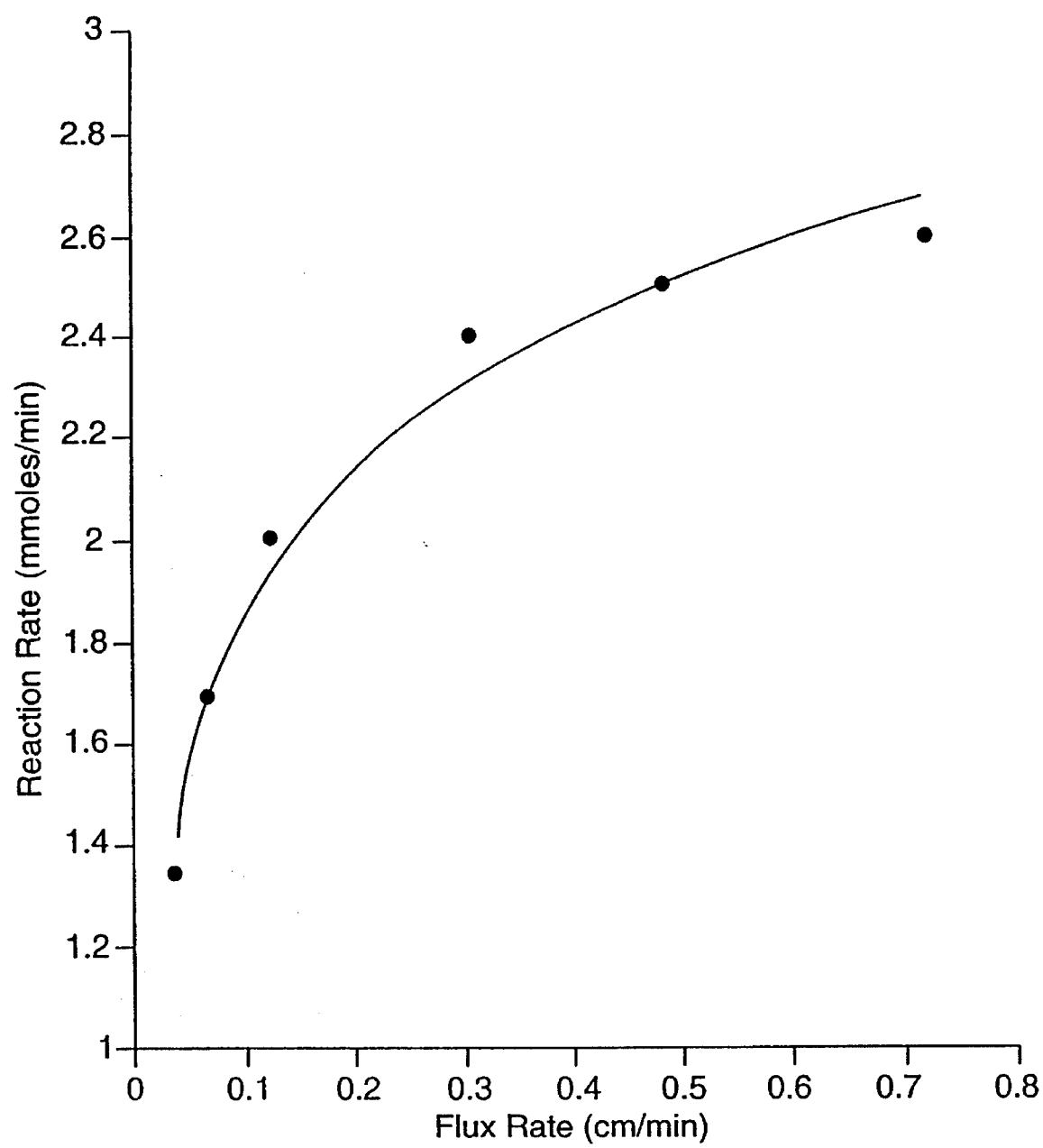
FIG. 9 is a graph showing reaction rate of hydrolysis of Penicillin G using the PGA cartridge versus flux rate of reaction solution through the cartridge.

The materials and procedures of Example 4 were utilized except that the following flux rates of reaction solution were utilized: 0.036, 0.068, 0.124, 0.307, 0.494, and 0.718 cm/minute; the first three flux rates were supplied by use of a smaller peristaltic pump, Masterflex Model 7520-00 (available from Cole Palmer Instrument Co., Chicago, Ill.). Initial reaction rates were determined at each flux rate and the initial reaction rates were plotted versus flux rate in FIG. 9. The data from these trials show that recycling flux rates in excess of 0.01 cm/minute were preferred, with flux rates in excess of 0.10 cm/minute being more preferred, and with flux rates in excess of 0.30 cm/minute being most preferred.

EXAMPLE 6

This example teaches that the enzyme could be insolubilized onto suitable particulates already loaded onto the upstream surface of a filter element. This is an important capability of the filtration layers of the present invention because manufacturing costs could be significantly reduced. Although "isolated" EMPHAZE particulates were utilized in the work below to document post-binding capability of enzymes, it is not necessary to employ "isolated" synthetic particulates such as EMPHAZE. An insoluble polymeric product can be loaded onto filter cartridges by pumping the polymer product slurry directly from the polymerization reactor to further reduce costs.

The loading procedure of Example 1 was repeated except no PGA was bound to the EMPHAZE particles loaded, and 10.0 grams of the particles were loaded at 4 L/minute flow rate. After loading, the cartridge was rinsed with 2 L of citrate buffer, and PGA (5.75 mL; 400 mg of the enzyme) was added to 660 mL of fresh citrate in a 2 L reaction reservoir. The resulting solution was pumped at 4 L/minute (flux rate=0.48 cm/minute) through the cartridge for 30 minutes. At this point the solution in the reservoir was analyzed for free PGA activity and less than 1% of the original challenge activity was detected. The cartridge was then rinsed with 10 L of 0.01 M phosphate/0.1M sodium chloride and then fitted as the catalyst filter assembly into the reaction system of FIG. 6 and Example 4. An initial rate of 2.09 mmoles/minute was observed or about 80% of the rate obtained with pre-immobilized particulates in Example 4.

EXAMPLE 7

This example shows synthetic utilization and reuse capability of the PLE cartridge of Example 2.

Figure 10:
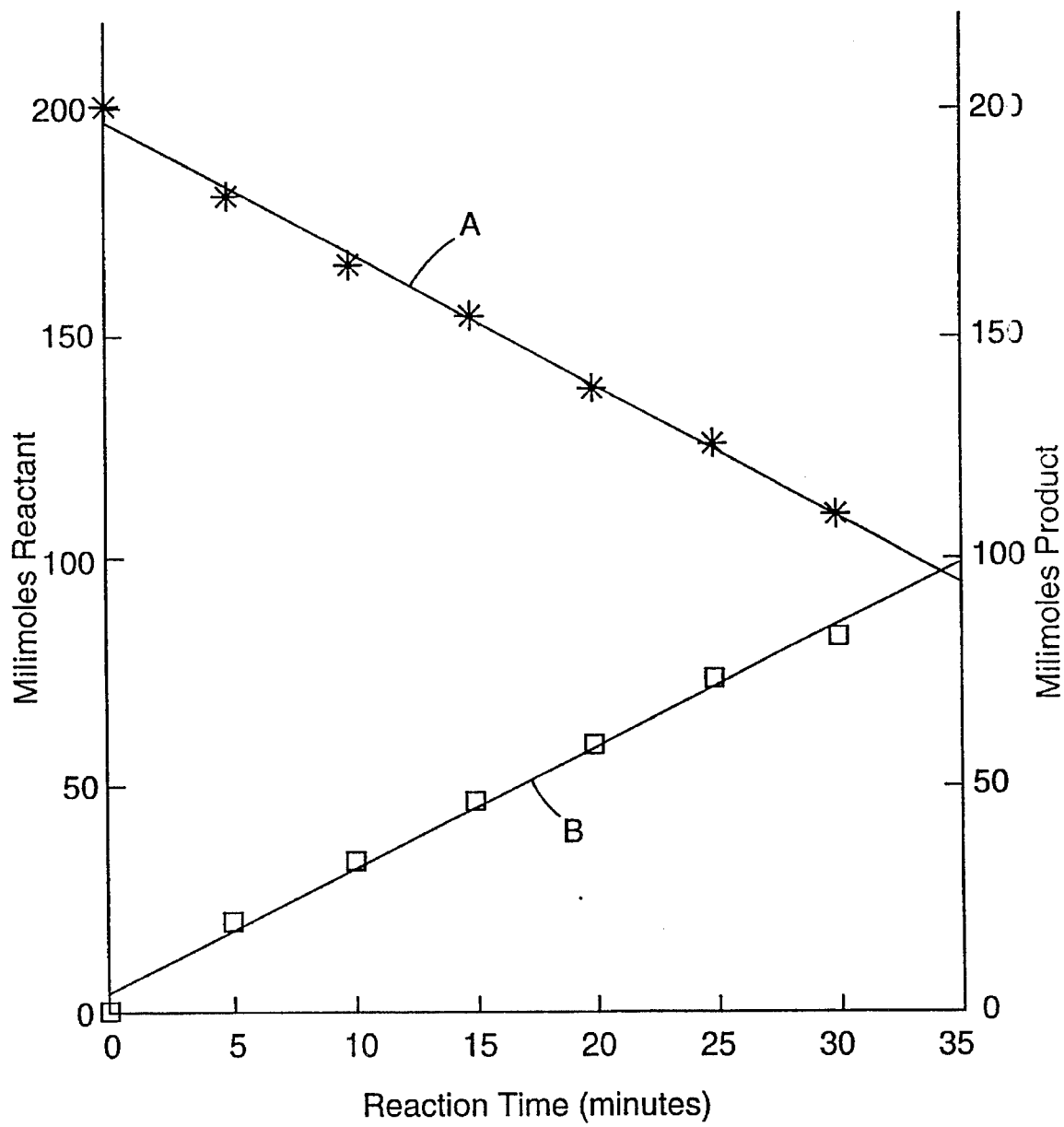
FIG. 10 is a dual graphic plot of the hydrolysis of propylene glycol methyl ether acetate (PGMEA) and its disappearance with time (line A) and a plot of the appearance of the 1-methoxy-2-propanol product with time (line B).

A simplified version of the reaction system of FIG. 6 was employed in which enough buffering capacity was present in the reaction solution so that no additional pH correcting titrant was required. Also, the reaction was conducted at room temperature so no external heating was needed. Propylene glycol methyl ether acetate (26.4 grams; 0.200 mole; available from Aldrich Chemical Co., Milwaukee, Wis.), 7.02 mL of N,N-dimethylacetamide (internal standard), and 4 L of 0.10M EPPS pH 8.0 buffer were added to the reaction reservoir. The pump was engaged at 3.8 L/minute (flux rate=0.45 cm/minute) and aliquots of the reaction solution were removed with time and evaluated for reactant and product content by capillary gas chromatography. The data in FIG. 10 show an important one-to-one correspondence between disappearance of reactant (line slope=−2.9) and appearance of product (line slope=+2.7); this shows that only the desired hydrolysis reaction was occurring. In subsequent runs with the PLE cartridge, the EPPS buffer was replaced by a less costly 0.10M phosphate buffer, and after 10 runs no loss in activity of the PLE cartridge was observed.

EXAMPLE 8

This example demonstrates that high flux rates had a beneficial effect on conversion with the PLE cartridge as well.

Figure 11:
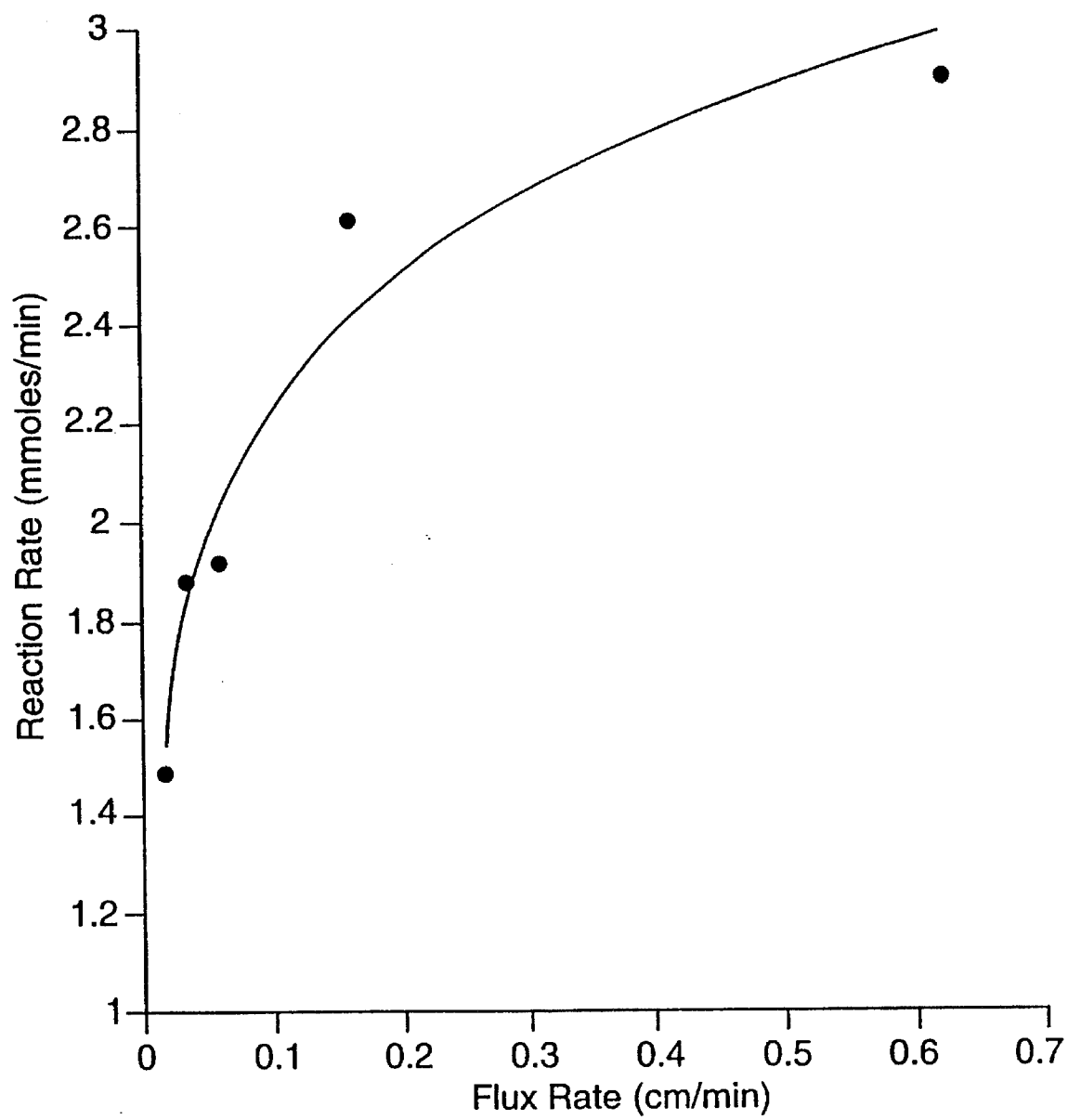
FIG. 11 is graphic plot of the initial rates of hydrolysis of PGMEA versus recycling flux rate.

The reaction system and method of Example 7 were utilized with the following flux rates: 0.021, 0.043, 0.064, 0.170, and 0.631 cm/minute. A plot of initial reaction rates versus flux rates in FIG. 11 shows that increased flux rates, as with the PGA cartridge of Example 5, have a beneficial effect on conversion, with preferred flux rates being at least 0.10 cm/minute and more preferably at least 0.30 cm/minute.

EXAMPLE 9

This example demonstrates the large scale synthetic utilization of the PLE cartridge. Previous efforts to obtain R-methyl 3-methylglutarate involving soluble PLE were conducted on 5 grams (3 days; J. B. Jones, et al., *J. Chem. Soc. Chem. Commun.*, 1984, 579) and 15 grams (overnight, C. Tamm, et al., *Helv. Chim. Acta.*, 1983, 66, 744) of starting dimethyl 3-methylglutarate (DMMG). In contrast, the PLE cartridge in this example provides the R-isomer hydrolysis product in greater than 99% optical yield and in 91.5% isolated chemical yield in less than 3 hours using 96.2 grams of DMMG.

Enantioselective Hydrolysis of Dimethyl 3-methylglutarate

The reaction system of FIG. 6 and prepared as in Example 1 was utilized except that the PLE cartridge of Example 2 was employed as catalyst filter assembly. Reaction was conducted by adding DMMG (25.0 grams; 0.143 mole; Aldrich) to the phosphate/chloride solution at pH 7.8. Progress of the hydrolysis reaction was monitored by observing the quantity of 1.00N sodium hydroxide titrant added to maintain constant pH; comparative runs were conducted over the timeframe of the entire reaction to show that no auto- or chemical hydrolysis of DMMG occurred at pH 7.8. Within 45 minutes the calculated amount of caustic had been added, so another 25.0 grams of DMMG were added; it was also noted that the hydrolysis reaction was slightly exothermic as reaction solution temperature had increased to 24° C. After a third portion of DMMG had been added and converted, a fourth portion was added for a total DMMG addition of 96.2 grams (0.552 mole). By this time the temperature of the reaction solution was 26° C., and the last few milliliters of caustic required a greater period of time to be added which was probably an indication of product inhibition finally appearing due to the accumulation of product from the beginning of the DMMG addition. Total reaction time was 144 minutes. The solution was pumped into a large separatory funnel, and the catalyst filter assembly was washed with 1700 mL of buffer solution which was also added to the aqueous product solution. This solution was washed with ether (1 L) and acidified to pH 2.37 by addition of 46 mL of concentrated hydrochloric acid. This was then extracted with ether (2×1500 mL) and continuously extracted with ether overnight. After drying (magnesium sulfate), ether was removed at reduced pressure to yield 80.8 grams of a colorless liquid (91.5% yield). The identity of the liquid as methyl 3-methylglutarate was confirmed by spectral analyses, and the optical purity was determined to be in excess of 99% by employing an NMR technique using a chiral solvent.

EXAMPLE 10

This example shows synthetic utilization of whole cells as the insolubilized enzyme particulates on the upstream surface of a compound radially pleated filter cartridge.

Baker's yeast (*Saccharomyces cerevisiae*) was obtained from a local grocery store and cultivated in 2 L of Potato Dextrose Broth (Difco, Detroit, Mich.) in a 3 L Erlenmeyer flask. After inoculation, the cells were incubated at 28° C. for 48 hours while being aerated and agitated in an environmental shaker. The final concentration of cells in the culture was approximately 2.5 billion cells per mL. The cells were harvested by centrifugation in a Sorvall RC5C Centrifuge (Dupont Analytical Instruments, Wilmington, Del.) at 3000 rpm for 1 hour, washed twice with phosphate buffered saline and collected between washes by centrifugation. The cells were harvested from the buffer by centrifugation, with the cell pellet being resuspended in 0.1M phosphate buffer pH 7.0. The reaction system of Example 7 was employed, with both packing and reaction procedures being conducted with a flux rate of 0.06 cm/minute. The buffer in the reaction solution reservoir was 0.1M phosphate buffer also containing glucose with an initial concentration of 0.86 wt %. Production of ethanol was monitored by gas chromatography, and after 52 hours ethanol conversion was 24.2%.

Various modifications and alterations of this invention will become apparent to those skilled in the art without departing from the scope of the invention.

We claim:

1. A filter element comprising a composite filtration medium having an upstream surface and a downstream surface, said composite filtration medium including a first layer comprising a porous fibrous filtration layer having an average pore size greater than 1 micrometer and up to 50 micrometers and a second layer consisting essentially of particulates selected from the group consisting of insoluble enzyme particulates and insoluble particulates comprising an enzyme, said second layer being located on the upstream surface of said first layer.

2. The filter element according to claim 1 wherein said filtration medium is a surface filtration medium.

3. The filter element according to claim 1 wherein said filtration medium is a depth filtration medium.

4. The filter element according to claim 1 wherein said fibrous filtration layer comprises one or a multiplicity of fibrous layers.

5. The filter element according to claim 4 wherein said one or multiplicity of fibrous layers is selected from the group consisting of polyamide, polyolefin, glass, cellulosics, polyester, and ceramics.

6. The filter element according to claim 5 wherein said fibrous layer is polypropylene.

7. The filter element according to claim 4 wherein said fibrous layer is a cellulosic.

8. The filter element according to claim 4 wherein said fibrous layer is nonwoven.

9. The filter element according to claim 1 wherein said insoluble particulates comprise a support on which is bound, adhered, or entrapped an enzyme.

10. The filter element according to claim 9 wherein said support for said particulates is selected from the group consisting of an azlactone functional support, an oxirane functional support, and an isocyanate functional support.

11. The filter element according to claim 9 wherein said enzyme is selected from the group consisting of Penicillin acylase, pig liver esterase, and glucose isomerase.

12. The filter element according to claim 1 wherein said insoluble particulates are insoluble in nonaqueous liquids.

13. The filter element according to claim 1 which is a compound radially pleated filter element.

14. The filter element according to claim 1 wherein said insoluble particulates on the upstream surface of said filtration layer are insoluble in aqueous media.

15. A filter cartridge comprising a filter element comprising a composite filtration medium having an upstream surface and a downstream surface, said composite filtration medium including a first layer having an average pore size greater than 1 micrometer and up to 50 micrometers comprising a porous fibrous filtration layer and a second layer consisting essentially of particulates selected from the group consisting of insoluble enzyme particulates and insoluble particulates comprising an enzyme, said second layer being located on the upstream surface of said first layer.

16. A catalyst filter assembly comprising the filter cartridge according to claim 15 in a housing, the filter cartridge being capable of effecting chemical conversion utilizing the insoluble enzyme particulates as catalyst.

17. A reaction system comprising the catalyst filter assembly according to claim 16 and at least a reaction solution contained in a reservoir, a pump, and connection tubing.

18. The filter cartridge according to claim 15 wherein said filtration medium of said filter element is a surface filtration medium.

19. The filter cartridge according to claim 15 wherein said filtration medium of said filter element is a depth filtration medium.

20. The filter cartridge according to claim 15 wherein said filtration layer of said filtration medium comprises one or a multiplicity of fibrous layers.

21. The filter cartridge according to claim 20 wherein said one or multiplicity of fibrous layers of said filtration medium is selected from the group consisting of polyamide, polyolefin, glass, cellulosics, polyester, and ceramics.

22. The filter cartridge according to claim 21 wherein said fibrous layer of said filtration medium is a cellulosic.

23. The filter cartridge according to claim 21 wherein said fibrous layer of said filtration medium is polypropylene.

24. The filter cartridge according to claim 15 wherein said fibrous layer filtration medium is nonwoven.

25. The filter cartridge according to claim 15 wherein said insoluble particulates of said filter medium comprise a support on which is bound, adhered, or entrapped an enzyme.

26. The filter cartridge according to claim 25 wherein said support for said particulates is selected from the group consisting of an azlactone functional support, an oxirane functional support, and an isocyanate functional support.

27. The filter cartridge according to claim 15 wherein said enzyme is selected from the group consisting of Penicillin acylase, pig liver esterase, and glucose isomerase.

28. The filter cartridge according to claim 15 wherein said insoluble particulates on said filtration layer are insoluble in nonaqueous liquids.

29. The filter cartridge according to claim 15 which comprises a compound radially pleated filter element.

30. The filter cartridge according to claim 15 wherein said insoluble particulates on the upstream surface of said filtration layer are insoluble in aqueous media.

31. A filter element comprising a composite filtration medium having an upstream surface and a downstream surface, said composite filtration medium including a first layer comprising a porous fibrous filtration layer having an average pore size greater than 1 micrometer and up to 50 micrometers and a second layer consisting essentially of particulates selected from the group consisting of insoluble enzyme particulates and insoluble particulates comprising an enzyme, said second layer being located on the upstream surface of said first layer, said filter element having a flow through rate of at least 833 mL/min. at a pressure of at most 0.25 MPa.

32. The filter element according to claim 31 whereto said flow rate is at least 2500 mL/min.

* * * * *